(12) United States Patent
Youngbull et al.

(10) Patent No.: US 10,238,587 B2
(45) Date of Patent: Mar. 26, 2019

(54) ERASABLE TATTOO INK AND METHOD FOR REMOVING TATTOOS

(71) Applicant: Excelsior Nanotech Corporation, Bellevue, WA (US)

(72) Inventors: Cody Youngbull, Tempe, AZ (US); Lixin Zheng, Kirkland, WA (US)

( * ) Notice: Subject to any disclaimer, the term of this patent is extended or adjusted under 35 U.S.C. 154(b) by 161 days.

(21) Appl. No.: 15/211,593

(22) Filed: Jul. 15, 2016

(65) Prior Publication Data
US 2017/0014317 A1    Jan. 19, 2017

Related U.S. Application Data

(60) Provisional application No. 62/192,954, filed on Jul. 15, 2015.

(51) Int. Cl.
| C09D 11/00 | (2014.01) |
| A61K 8/02 | (2006.01) |
| A61K 8/19 | (2006.01) |
| A61K 8/81 | (2006.01) |
| A61Q 1/02 | (2006.01) |
| A61Q 1/14 | (2006.01) |
| A61Q 19/02 | (2006.01) |

(52) U.S. Cl.
CPC .............. *A61K 8/19* (2013.01); *A61K 8/0245* (2013.01); *A61K 8/8141* (2013.01); *A61Q 1/025* (2013.01); *A61Q 1/145* (2013.01); *A61Q 19/02* (2013.01); *A61K 2800/413* (2013.01); *A61K 2800/43* (2013.01); *A61K 2800/62* (2013.01)

(58) Field of Classification Search
CPC ........ C09D 11/00; A61K 8/19; A61K 8/0245; A61K 8/8141; A61K 2800/413; A61K 2800/43; A61K 2800/62; A61Q 1/025; A61Q 1/145
USPC ................................ 106/31.03, 31.32, 31.64
See application file for complete search history.

(56) References Cited

U.S. PATENT DOCUMENTS

| 6,013,122 | A | * | 1/2000 | Klitzman | ............... | C09D 11/00 |
| | | | | | | 106/31.03 |
| 6,800,122 | B2 | * | 10/2004 | Anderson | ............. | C09D 11/00 |
| | | | | | | 106/31.03 |
| 9,365,659 | B2 | * | 6/2016 | Youngbull | ........... | G01N 33/442 |
| 2005/0172852 | A1 | * | 8/2005 | Anderson | ............. | C09D 11/50 |
| | | | | | | 106/31.03 |
| 2005/0203495 | A1 | * | 9/2005 | Malak | .................... | A61Q 1/145 |
| | | | | | | 606/9 |
| 2009/0311295 | A1 | * | 12/2009 | Mathiowitz | ............. | A61Q 1/02 |
| | | | | | | 424/401 |

* cited by examiner

*Primary Examiner* — Helene Klemanski
(74) *Attorney, Agent, or Firm* — Glenn H. Lenzen; Dietze and Davis, P.C.

(57) ABSTRACT

An improved erasable tattoo ink and a method and apparatus for removing tattoos using an energy transfer photodisruptive mechanism whereby efficiency of the transfer of energy from a low energy light source to a higher energy donor and then to a tattoo pigment molecule for photodecomposition of the ink color pigmentation is optimized.

39 Claims, 1 Drawing Sheet

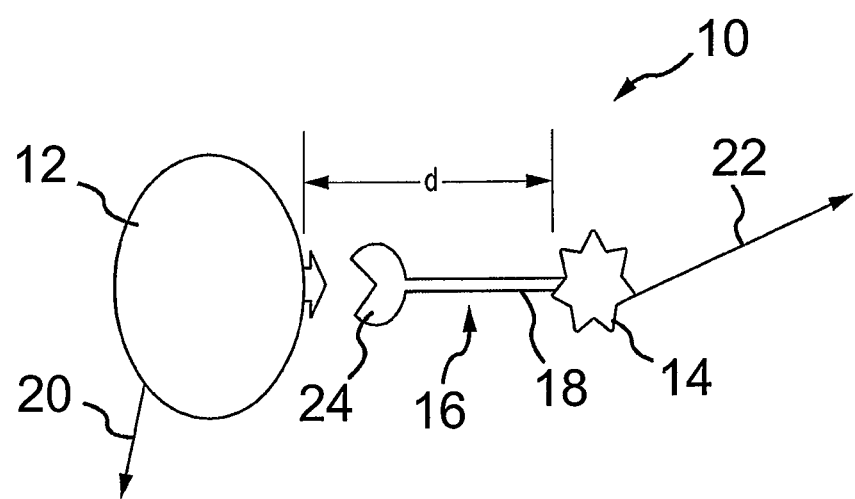

ERASABLE TATTOO INK AND METHOD FOR REMOVING TATTOOS

CROSS-REFERENCE TO RELATED APPLICATIONS

This application claims the benefit of U.S. Provisional Patent Application Ser. No. 62/192,954, filed on Jul. 15, 2015, and entitled ERASABLE TATTOO INK AND METHOD AND APPARATUS FOR REMOVING TATTOOS, which is incorporated herein by reference.

FIELD OF THE INVENTION

The present invention relates generally to dermatological treatment using nanotechnological and photonic processing systems and methodologies for skin pigmentation treatment and removal. More particularly, the present invention relates to an erasable tattoo ink and a method for removing tattoos.

BACKGROUND OF THE INVENTION

Tattooing is a widespread and increasingly popular practice of decorating an individual's skin via the injection of colored pigment dispersed in tattoo ink into the skin into small holes formed therein by a tattoo device or needle. Millions of individuals around the world have at least one permanent tattoo, and with the current popularity of so-called "body art", more and more young men and women of an average age of 18 years are acquiring tattoos. Depending upon the area of the body being tattooed, the artwork may or may not be easily concealed by clothing, and tattoos acquired in youth may become embarrassing in later life and create an impediment to employment opportunities and overall social acceptance. Accordingly, a substantial commercial market for tattoo removal has developed.

Tattoo removal is a more difficult, painful and, quite possibly, more expensive process than the initial application of the tattoo itself which entails injecting pigments of various colors into the dermis. The dermis is the skin layer which lies immediately beneath the approximately 1 mm thick epidermis—the dead, outer external surface skin layer. In newly applied tattoos, the ink pigments tend to aggregate near the upper dermis close to the epidermis, and early techniques for tattoo removal used abrasives to abrade away the epidermis above the tattoo pigment to reach and abrade away the pigment itself. Clearly, this technique is painful and may expose a subject to infection and permanent scarring. Moreover, over time, the tattoo pigments may become encapsulated in fibroblasts and migrate deeper into the dermis, making older tattoos more difficult to remove by abrasion.

With the discovery of the laser, a non-abrasive technique became available for tattoo removal. Experiments with the application of laser energy to permanent ink tattoos were performed in the late 1960's using continuous wave argon and later carbon dioxide lasers, which, in effect, burned off the tattoo. The undesirable but foreseeable side effect of these painful processes was permanent scarring in the former location of the tattoo.

In the late 1980's the development of pulsed or Q-switched lasers provided a commercially practical technique for the treatment of various dermatological pigmentation issues, including the removal of tattoos. Q-switching is a technique for obtaining high energy nanosecond pulses of laser energy from solid-state lasers, and by selecting the laser energy wavelength or color so that the tattoo ink pigment absorbs the laser energy more readily than the surrounding skin, the tattoo may be removed by thermal photo ablation. At sufficient energy levels, the laser pulses cause the thousands of particles of tattoo pigment in the skin to heat up and photo ablate or fragment into smaller pieces as a result of the inherent thermal shock waves generated by the laser energy. The pigment fragments are normally no longer colored and are then diffusibly removed by normal body processes.

Since tattoo pigments cover a wide range of colors, no single laser wavelength is suitable for tattoo removal by photo ablation. The selective ablation of ink pigments depends upon four factors:

The color of the laser energy must penetrate sufficiently deep into the skin to reach the tattoo pigment.

The color of the laser energy must be selected such that it is more highly absorbed by the tattoo pigment than by the surrounding skin tissue-accordingly, different tattoo pigments require different laser colors.

Laser energy pulse duration must be very short so that the tattoo pigment is heated to fragmentary temperature before its heat can dissipate to the surrounding tissue so as to prevent scarring.

Sufficient energy must be delivered during each laser pulse to heat the pigment to fragmentation. Otherwise, no removal will occur.

The application of laser energy to and the resulting heating of the skin and the formation of highly localized thermal shock waves in the dermis are the principal sources of trauma in the laser treatment and removal of tattoos. Typically, more than one treatment is necessary to remove the entire tattoo, and the procedures are painful, expensive and may result in permanent scarring and/or pigment color variations after the healing process is completed.

Various attempts have been made to develop a less painful and less costly method of removing or at least concealing permanent ink tattoos. One such method disclosed in U.S. Pat. No. 5,833,649 issued to Atef on Nov. 10, 1998, for Method and Kit for Disguising Tattoos, teaches a method of concealing tattoos on an individual which includes the steps of adding various coloring pigments to tattooing ink until a color which matches the person's skin color is attained. The colored ink is brushed over the brushed over the tattoo to conceal it. It may be made permanent by injecting the skin-colored ink into the tattoo. However, this method does not affect permanent removal of the tattoo and must be repeated on a regular basis to maintain the concealment.

Malak discloses Methods and Devices for Plasmon Enhanced Medical and Cosmetic Procedures in U.S. Patent Application Publication No. US 2005/0203495 published Sep. 15, 2005, which suggests that a method of tissue ablation using nanosecond pulses of laser energy which exhibit strong electromagnetic fields may be used in conjunction with magnetic nano bodies injected into the dermis in close proximity to the tattoo ink pigment particles. The laser energy pulses interact with the nano particles to release surface plasmon resonance (SPR) illumination to effectively photodecompose the pigment. Nonetheless, Malak's approach is at this stage theoretical in concept and involves an undisclosed number of painful injections into a tattoo to be effective.

More recently, Smits et al. in U.S. Patent Application Publication No. 2012/0215209, for Tattoo Removal and Other Dermatological Treatments Using Multi-Photon Processing, published Aug. 23, 2012, disclose a system and method for removing a portion of a tattoo using a relatively low energy, multi-photon intense pulse of light to ablate the tattoo ink in a highly localized area. While the Sits et al. process claims to minimize surrounding tissue damage, it does not eliminate it, and the process still requires multiple passes to effectively remove a tattoo.

In view of the foregoing, a tattoo removal system and method is needed which provides for effective, painless, scar-free tattoo removal which may be accomplished economically in a single session without the need for multiple treatments.

SUMMARY OF THE INVENTION

Accordingly, the present invention provides an improved erasable tattoo ink and a method and apparatus for removing tattoos using an energy transfer photodisruptive mechanism whereby efficiency of the transfer of energy from a low energy light source to higher energy donor and then to a tattoo pigment molecule for photodecomposition of the ink color pigmentation is optimized.

In accordance with an embodiment, the efficiency of the energy transfer is optimized by providing surface treated upconverting nanocrystal donors for near infrared (NIR) to blue and ultraviolet (UV) upconversion which are stably miscible in a tattoo ink.

In yet another embodiment of the present invention the upconverting nanocrystal donors comprise sodium yttrium fluoride ($NaYF_4$) nanocrystals doped with Rare Earth elements.

In another embodiment, the efficiency of the energy transfer from the upconverting nanocrystal donors to the initiator/acceptors is increased by resonantly coupling the energy stored in the donor to the initiator via Förster Resonance Energy Transfer (FRET).

In yet another embodiment, the upconverting initiator/acceptors are sensitive to blue light and UV radiation.

In still another embodiment of the present invention, the FRET efficiency is optimized by controlling the distance between the donor and the initiator/acceptor; controlling the spectral overlap of the donor emission spectrum and the acceptor absorption spectrum; and by controlling the relative orientation of the donor emission dipole moment and the acceptor absorption dipole moment.

In another embodiment of the present invention, the photodecomposition process is initiated by exposing the tattooed area of the skin to a source of ultraviolet energy.

These and other objects of the present invention will be apparent from the accompanying description of the invention and supplemental supporting materials provided herein.

BRIEF DESCRIPTION OF THE DRAWINGS

The FIGURE is a side view of an energy transfer photopolymerization system suspended in an erasable tattoo ink in accordance with an embodiment of the present invention.

DESCRIPTION OF THE INVENTION

It should be noted that the present description is by way of illustration only, and that the concepts and examples presented herein are not limited to use or application of any single erasable tattoo ink or method and apparatus for tattoo removal. Hence, while the details of the tattoo ink, and method and apparatus for tattoo removal described herein are for the convenience of illustration and explanation with respect to the exemplary embodiments, the principles disclosed may be applied to other types of methods and systems for the treatment of various dermatological pigmentation issues without departing from the scope of the present invention.

By way of reference, the erasable tattoo ink and method and apparatus for tattoo removal herein disclosed expands upon the principles disclosed in U.S. Pat. No. 9,365,659 B2 issued Jun. 14, 2016 to the Applicant for the present invention and titled, System and Method for Optimizing the Efficiency of Photo-Polymerization, the contents of which are incorporated herein by reference. The present invention incorporates Applicant's unique and novel ultraviolet (UV) emitting upconverting nanocrystals (also referred to herein as UNC's) in a tattoo ink prior to the application of a tattoo on an individual's skin.

Should the individual at some point in the future decide to have the tattoo removed, the novel features of the erasable ink and methods of the present invention take advantage of the so-called "near infrared window in biological tissues", also known in the art as an optical or therapeutic window having a range of wavelengths from 650 to 1350 nm, where light has its maximum depth penetration in tissue. As discussed in the literature, within the NIR window, scattering is the most dominant light-tissue interaction and the propagating light becomes diffused rapidly, and the probability of photon absorption increases. The technique using this window is called near infra-red spectroscopy (NIRS), and medical imaging techniques such as fluorescence image-guided surgery make use of the NIR window to detect various structures within the body.

More specifically, a person desiring to have a tattoo removed would have his or her skin exposed to an intense near infrared (NIR) or infrared (IR) light source. The intensity of the light must be determined on a case by case basis and is a function of the individual's skin color, skin condition, and tattoo depth. The light source may be either continuous (CW) or pulsed. The NIR or IR energy will interact less with the patient tissue than with the pigment dye molecule of the tattoo. The system and method of the present invention also introduces significantly less heat into the individual's skin than current tattoo removal methods, thus reducing the individual's level of discomfort and minimizing, if not eliminating scarring. The increased absorption cross-section of the dye relative to the patient's skin is a key factor in the overall effectiveness of this process.

Exposing a tattoo made using the erasable ink of the present invention to ultraviolet light from a suitable source, by way of example and not of limitation, upconverting nanocrystals in the tattoo ink, effectively erases the tattoo. Directing the energy of a near infrared laser, via the near infrared window, into the tattooed tissue, initiates the emission of higher energy ultraviolet (UV) radiation via the upconverting nanocrystals in the tattoo ink suspension deposited in the subject's dermis, as will be described in greater detail below. The UV energy effects removal of the tattoo via several mechanisms or a combination of mechanisms.

One mechanism is referred to as photobleaching, also known as fading. Photobleaching is the photochemical alteration of a dye or a fluorophore molecule such that it is permanently unable to fluoresce. Permanent photobleaching is caused by cleaving of covalent bonds or non-specific reactions between a fluorophore and surrounding molecules in the ink suspension. The process effectively bleaches the color pigment of the tattoo ink, thereby degrading any visible color and effectively "erasing" the tattoo much more effectively, rapidly, and completely without any damage to adjacent tissue and resultant scarring and with less pain and expense than any prior art ablation or abrasive tattoo removal techniques.

Another mechanism involves photodissociation, photolysis or photodecomposition which is any process by which a chemical compound is broken down by light. A third mechanism includes a process of photocleavage of specifically designed groups in a pigment molecule in the erasable ink suspension.

At the subatomic level, an erasable tattoo ink of the instant invention comprises a suspension of a preselected visible color pigment; at least one supramolecular upconverting nanoparticle structure surface treated with a ligand coating, whereby the nanoparticle structure is uniformly soluble and stably miscible in the suspension. The supramolecular structure of an exemplary nanocrystal of the present invention is illustrated in the FIGURE Supramolecular chemistry refers to the domain of chemistry beyond that of molecules and focuses on the chemical systems made up of a discrete number of assembled subunits, functional groups and moieties. In organic chemistry, functional groups are specific groups of atoms or bonds within molecules that are responsible for the characteristic chemical reactions of those molecules. The term "moiety" is often used interchangeably with "functional group"; however, the preferred definition is that a moiety is part of a molecule that may include either whole functional groups or parts of functional groups as substructures. For the purposes of this invention, the above-referenced definitions will apply to those terms as used herein. It is via the selective incorporation of multi-functional nanocrystalline structures and terminated moieties possessing desired physical properties specific to the pigments of the erasable inks of the present invention that the unique tattoo removal processes are achieved.

Referring now to the FIGURE, elements of the system for energy transfer photobleaching or photodissociation of the pigments in the erasable ink suspensions of the present invention are shown in greater detail. A supramolecular nanoparticle structure is shown generally at 10 and includes an upconverting nanoparticle/nanocrystal energy donor 12, a photoinitiator or energy acceptor 14 located a preselected intramolecular distance, d, from the donor, and means 16 for linking the donor 12 to the acceptor 14, the linking means being structured and arranged to establish and maintain the intramolecular distanced in a preferred range of approximately 1 to approximately 20 nanometers so as to optimize the energy transfer there between. The energy donor is adapted to release energy stored therein in response to exposure to energy having a first preselected wavelength (represented graphically by arrow 20), and the acceptor is structured and arranged to release energy having a second, different preselected wavelength (represented graphically by arrow 22) in response to the resonant transfer of energy from the donor to the acceptor. The released energy 22 interacts with the color pigment in the ink, whereby the color is effectively "erased' without causing undue discomfort to or scarring of the individual undergoing the process.

The system and method of the present invention optimizes the efficiency of the energy transfer from the upconverting nanocrystal donors to the initiator/acceptors by resonantly coupling the energy stored in the donor to the initiator via Förster Resonance Energy Transfer (FRET). FRET is fundamentally non-radiative and, as such, the upconverted (visible blue or UV) photon is never actually produced. Rather, its energy is resonantly transferred to a light absorbing moiety (in this case the photoinitator) in the supramolecular structure comprised of the nanocrystal-ligand-photoinitiator. This is critically different from the systems and methods of the prior art wherein the upconverted photon is produced in reality and then propagated toward a photoinitiator. In the later, the real photon is absorbed by the intervening ink suspension material, and only a small fraction of the time the photoinitiator actually absorbs the real photon. Hence, the process is extremely inefficient.

A main concern associated with prior art systems is the lack of compatibility or miscibility of the supramolecular upconverting system with existing polymer systems. Accordingly, in accordance with an embodiment of the present invention, the multi-functional nanocrystalline polymer additive donors described herein are inorganic rare earth elements which are surface-treated or ligand-coated/passivated, as that term is used in the art, to make them miscible (dissolved or stably and uniformly suspended) in existing polymer systems, such as an erasable tattoo ink of the present invention. The rare earth elements are selected from the group consisting of Erbium (Er), Ytterbium (Yb), Thulium (Tm) and Europium (Eu). Preferably, each of the donors comprises a submicron nanoparticle, the nanoparticle being selected from the group of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, $SiO_2$, and alloys and layers thereof.

In addition to selectively controlling and maintaining the intramolecular distance or spacing d between the donor and the acceptor, the resonant energy transfer efficiency may be further optimized by judicious selection and matching of the respective energy emission and energy absorption spectra of the donor and the acceptor and, to the extent possible, the relative orientations of the donor with respect to the acceptor. A donor will have an energy emission spectrum of a known spectral range, and an acceptor will have an absorption spectrum of a known spectral range. By selecting the donor and the acceptor such that the energy emission spectrum and the energy absorption spectrum bandwidths at least partially overlap, the efficiency of the energy transfer between the two elements, and therefore the efficiency of the NIR photo-polymerization photoinitiation process will be optimized.

The acceptor may be selected from the group of compounds comprising photo-acid generators or free radical generators. In a preferred embodiment, the acceptor may be selected from the group consisting of Azobisisobutyronitrile (AIBN), Benzoyl peroxide, Camphorquinone, Trimethyl-benzoyl-diphenylphosphine oxide, Phenyl propanedione, Ethyl dimethylamino benzoate, Dihydroxyethyl-para-toluidine, dimethylaminoethyl methacrylate, Irgacure, Irgacure PAG, or CGI.

Referring again to the FIGURE, the linking means preferably comprises an organic or an inorganic molecule 18 operatively connected to both the donor and the acceptor. By way of example and not of limitation, the linker may be in the form of an organic molecule such as an alkyl chain, a hydrophobic or hydrophilic oligomer, preferably a sub 20 nm molecule. The linking means 16 further includes a terminated moiety 24 structured and arranged to bind the linking means to the donor 12, the terminated moiety being selected from the group of terminated moieties consisting of amine-terminated, hydroxyl-terminated, phosphoric-terminated, aldehyde-terminated, pyridine-terminated, and carboxylic acid-terminated moieties.

Changes may be made in the above methods, devices and structures without departing from the scope hereof. It should thus be noted that the matter contained in the above description and supporting materials should be interpreted as illustrative and not in a limiting sense. The following claims are intended to cover all generic and specific features described herein, as well as all statements of the scope of the present method, device and structure, which, as a matter of language, might be said to fall there between.

What is claimed is:

1. An erasable tattoo ink comprising:
a suspension including a preselected visible color pigment;
at least one supramolecular upconverting nanoparticle structure surface treated with a ligand coating, whereby the nanoparticle structure is uniformly soluble and stably miscible in the suspension, the nanoparticle structure including:
at least one upconverting nanoparticle energy donor adapted to release energy having a first preselected wavelength in response to exposure to energy having a wavelength falling in the near infrared or infrared spectrum;
at least one photo-initiating, energy absorbing acceptor moiety located at a preselected intramolecular distance d from the at least one energy donor, the photo-initiating moiety being adapted to receive the energy released by the at least one energy donor;
a molecule adapted to link the at least one energy donor to the at least one acceptor moiety, the linking molecule being structured and arranged to establish and maintain the preselected intramolecular distance between the at least one energy donor and the at least one acceptor moiety; and
a terminated moiety structured and arranged to bind the linking molecule to the energy donor and to control the relative orientation of the energy donor with respect to the acceptor moiety, the terminated moiety being selected from the group of terminated moieties consisting of amine-terminated, hydroxyl-terminated, phosphoric-terminated, aldehyde-terminated, pyridine-terminated, and carboxylic acid-terminated moieties;
whereby the relative orientation of the energy donor with respect to the acceptor moiety and the preselected intramolecular distance d cooperate with one another to optimize the resonantly-coupled, non-radiative energy transfer from the energy donor to the acceptor moiety; and;
wherein the at least one acceptor moiety is structured and arranged to release energy having a second preselected wavelength in response to the resonant transfer of energy from the donor to the acceptor moiety, the released energy be adapted to photo bleach or degrade the visible color pigment of the ink.

2. The ink of claim 1 wherein the at least one donor includes at least one rare earth element.

3. The ink of claim 2 wherein the rare earth element is selected from the group consisting of Erbium (Er), Ytterbium (Yb), Thulium (Tm) and Europium (Eu).

4. The ink of claim 2 wherein the donor comprises a submicron nanoparticle, the nanoparticle being selected from the group of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, and alloys and layers thereof.

5. The ink of claim 1 wherein the molecule linking the at least one energy donor to the at least one acceptor moiety comprises an organic molecule.

6. The ink of claim 5 wherein the organic molecule comprises an alkyl chain.

7. The ink of claim 1 wherein the molecule linking the at least one energy donor to the at least one acceptor moiety comprises an inorganic molecule.

8. The ink of claim 5 wherein the linking molecule comprises a sub 20 nm molecule.

9. The ink of claim 7 wherein the linking molecule comprises a sub 20 nm molecule.

10. The ink of claim 8 wherein the molecule linking the at least one energy donor to the at least one acceptor moiety comprises a hydrophobic or hydrophilic oligomer.

11. The ink of claim 1 wherein the preselected intramolecular distance d is in the range of approximately 1 nm to approximately 20 nm.

12. The ink of claim 1 wherein the acceptor moiety is a photo-acid generator.

13. The ink of claim 1 wherein the acceptor moiety is a free radical generator.

14. The ink of claim 1 wherein the acceptor moiety is selected from the group consisting of azobisisobutyronitrile (AIBN), benzoyl peroxide, camphorquinone, trimethylbenzoyl-diphenylphosphine oxide, phenyl propanedione, ethyl dimethylamino benzoate, dihydroxyethyl-para-toluidine, or dimethylaminoethyl methacrylate.

15. The ink of claim 1 wherein the at least one acceptor moiety is structured and arranged to release energy having a second preselected wavelength in response to the resonant transfer of energy from the donor to the acceptor moiety.

16. The ink of claim 15 wherein the donor includes an energy emission spectrum of a first spectral range.

17. The ink of claim 16 wherein the acceptor moiety includes an absorption spectrum of a second spectral range.

18. The ink of claim 17 wherein the first and second spectral ranges at least partially overlap.

19. The ink of claim 1 wherein the at least one donor comprises a submicron nanoparticle, the nanoparticle being selected from the group of $TiO_2$, $SiO_2$ and alloys and layers thereof.

20. An erasable tattoo ink comprising:
a suspension including a preselected visible color pigment;
at least one supramolecular upconverting nanoparticle structure surface treated with a ligand coating, whereby the nanoparticle structure is uniformly soluble and stably miscible in the suspension, the nanoparticle structure including:
at least one upconverting nanoparticle energy donor adapted to release energy having a first preselected wavelength in response to exposure to energy having a wavelength falling in the near infrared or infrared spectrum;
at least one photo-initiating, energy absorbing acceptor moiety located at a preselected intramolecular distance d from the at least one energy donor, the photo-initiating moiety being adapted to receive the energy released by the at least one energy donor, the acceptor moiety being selected from the group consisting of azobisisobutyronitrile (AIBN), benzoyl peroxide, camphorquinone, trimethylbenzoyl-diphenylphosphine oxide, phenyl propanedione, ethyl dimethylamino benzoate, dihydroxyethyl-para-toluidine, or dimethylaminoethyl methacrylate;
a molecule adapted to link the at least one energy donor to the at least one acceptor moiety, the linking molecule being structured and arranged to establish and maintain the preselected intramolecular distance between the at least one energy donor and the at least one acceptor moiety; and a terminated moiety structured and arranged to bind the linking molecule to the energy donor and to control the relative orientation of the energy donor with respect to the acceptor moiety;

whereby the relative orientation of the energy donor with respect to the acceptor moiety and the preselected intramolecular distance d cooperate with one another to optimize the resonantly-coupled, non-radiative energy transfer from the energy donor to the acceptor moiety; and;

wherein the at least one acceptor moiety is structured and arranged to release energy having a second preselected wavelength in response to the resonant transfer of energy from the donor to the acceptor moiety, the released energy be adapted to photo bleach or degrade the visible color pigment of the ink.

21. The ink of claim 20 wherein the at least one donor includes at least one rare earth element.

22. The ink of claim 21 wherein the rare earth element is selected from the group consisting of Erbium (Er), Ytterbium (Yb), Thulium (Tm) and Europium (Eu).

23. The ink of claim 21 wherein the donor comprises a submicron nanoparticle, the nanoparticle being selected from the group of $Y_2O_3$, $Y_2O_2S$, $NaYF_4$, $NaYbF_4$, YAG, YAP, $Nd_2O_3$, $LaF_3$, $LaCl_3$, $La_2O_3$, $LuPO_4$, $YVO_4$, $YbF_3$, $YF_3$, Na-doped $YbF_3$, and alloys and layers thereof.

24. The ink of claim 20 wherein the at least one donor comprises a submicron nanoparticle, the nanoparticle being selected from the group of $TiO_2$, $SiO_2$ and alloys and layers thereof.

25. The ink of claim 20 wherein the molecule linking the at least one energy donor to the at least one acceptor moiety comprises an organic molecule.

26. The ink of claim 25 wherein the organic molecule comprises an alkyl chain.

27. The ink of claim 20 wherein the molecule linking the at least one energy donor to the at least one acceptor moiety comprises an inorganic molecule.

28. The ink of claim 25 wherein the linking molecule comprises a sub 20 nm molecule.

29. The ink of claim 27 wherein the linking molecule comprises a sub 20 nm molecule.

30. The ink of claim 28 wherein the molecule linking the at least one energy donor to the at least one acceptor moiety comprises a hydrophobic or hydrophilic oligomer.

31. The ink of claim 20 wherein the terminated moiety is selected from the group of terminated moieties consisting of amine-terminated, hydroxyl-terminated, phosphoric-terminated, aldehyde-terminated, pyridine-terminated, and carboxylic acid-terminated moieties.

32. The ink of claim 20 wherein the preselected intramolecular distance d is in the range of approximately 1 nm to approximately 20 nm.

33. The ink of claim 20 wherein the acceptor moiety is a photo-acid generator.

34. The ink of claim 20 wherein the acceptor moiety is a free radical generator.

35. The ink of claim 20 wherein the at least one acceptor moiety is structured and arranged to release energy having a second preselected wavelength in response to the resonant transfer of energy from the donor to the acceptor moiety.

36. The ink of claim 35 wherein the donor includes an energy emission spectrum of a first spectral range.

37. The ink of claim 35 wherein the acceptor moiety includes an absorption spectrum of a second spectral range.

38. The ink of claim 37 wherein the first and second spectral ranges at least partially overlap.

39. An erasable tattoo ink comprising:

a suspension including a preselected visible color pigment;

at least one upconverting particle structure surface treated with a ligand coating, whereby the particle structure is uniformly soluble and/or stably miscible in the ink suspension, the particle structure including:

at least one upconverting particle energy donor adapted to release energy having a first preselected wavelength in response to exposure to energy having a wavelength falling in the near infrared or infrared spectrum;

at least one photo-initiating, energy absorbing acceptor moiety located at a preselected intramolecular distance d from the at least one energy donor, the photo-initiating/ . . . moiety being adapted to receive the energy released by the at least one energy donor;

a molecule adapted to link the at least one energy donor to the at least one acceptor moiety, the linking molecule being structured and arranged to establish and maintain the preselected intramolecular distance between the at least one energy donor and the at least one acceptor moiety; and a terminated moiety structured and arranged to bind the linking molecule to the energy donor and to control the relative orientation of the energy donor with respect to the acceptor moiety, the terminated moiety being selected from the group of terminated moieties consisting of amine-terminated, hydroxyl-terminated, phosphoric-terminated, aldehyde-terminated, pyridine-terminated, and carboxylic acid-terminated moieties;

whereby the relative orientation of the energy donor with respect to the acceptor moiety and the preselected intramolecular distance d cooperate with one another to optimize the resonantly-coupled, non-radiative energy transfer from the energy donor to the acceptor moiety; and;

wherein the at least one acceptor moiety is structured and arranged to release energy having a second preselected wavelength in response to the resonant transfer of energy from the donor to the acceptor moiety, the released energy be adapted to photo bleach or degrade the visible color pigment of the ink.

* * * * *